United States Patent [19]

Rudtke

[11] 3,942,523
[45] Mar. 9, 1976

[54] REINFORCED DOUBLE-FENESTRATED SURGICAL DRAPE

[75] Inventor: Helen T. Rudtke, Medford, N.Y.

[73] Assignee: American Hospital Supply Corporation, Evanston, Ill.

[22] Filed: Jan. 17, 1975

[21] Appl. No.: 541,870

[52] U.S. Cl. ............................................. 128/132 D
[51] Int. Cl.² ............................................ A61F 13/00
[58] Field of Search ............ 128/132 D, 132 R, 292, 128/275.1, 82.1

[56] References Cited
UNITED STATES PATENTS

| | | | |
|---|---|---|---|
| 3,503,391 | 3/1970 | Melges | 128/132 D |
| 3,799,161 | 3/1974 | Collins | 128/132 D |
| 3,856,006 | 12/1974 | Krzewinski | 128/132 D |
| 3,862,632 | 1/1975 | Hinsch | 128/132 D |

Primary Examiner—Lawrence W. Trapp
Attorney, Agent, or Firm—Dawson, Tilton, Fallon & Lungmus

[57] ABSTRACT

A double-fenestrated surgical drape, especially suitable for use in those operations requiring entry through both the abdominal wall and the perineum, comprising a pair of rectangular non-woven cellulosic sheets of unequal size joined together in overlapping relation to provide a narrow reinforced zone of increased thickness interposed between the fenestrations of the respective sheets.

7 Claims, 3 Drawing Figures

REINFORCED DOUBLE-FENESTRATED SURGICAL DRAPE

BACKGROUND AND SUMMARY

Of the surgical procedures requiring both peripheral and abdominal entry, some typical examples are abdominal hysterectomy with vaginal plasty, superapubic prostatectomy, laparascopy or peritoneoscopy, tubal ligation, and abdominoperineal resection. In some cases the procedures are performed concurrently by two surgical teams and in all instances proper asceptic technique requires separate fenestrations for the perineal and abdominal areas. While double-fenestrated paper drapes have been known in the past, such drapes have not been well suited for all of such operative procedures, especially those in which distorting forces of substantial magnitude are likely to be imposed on the edge portions defining the fenestrations of the drapes. Should the bridging connection between two fenestrations become broken during surgery, cross contamination would become a real possibility and redraping of the patient would become necessary, thereby interrupting and extending the operative procedure.

This invention involves a recognition of the problem and the discovery of a highly effective solution to it. The result is a multipurpose reinforced double-fenestrated surgical drape formed from non-woven cellulosic material (paper) which is capable of remaining intact despite the forces that might normally be applied to it during any of a variety of abdominal perineal operative procedures. More specifically, the drape is formed from two sheets of such material, one of the sheets having a narrow portion along one marginal edge which is secured in overlapping relation to a like portion of the other sheet to provide a laminated zone of mutual reinforcement. The sheets have a pair of elongated fenestrations arranged in longitudinal alignment on opposite sides of the reinforced zone, each sheet having its fenestration immediately adjacent to the marginal edge of the other sheet. In the disclosed embodiment, each of the sheets is generally rectangular in shape, one being substantially wider than the other, and is symmetrically oriented with respect to the longitudinal midline of the drape as a whole. The laminated zone of reinforcement extends across that midline and the elongated fenestrations extend along it. Such fenestrations are generally rectangular in shape, each fenestration having one end edge immediately adjacent the laminated zone of reinforcement. The result is a relatively inexpensive paper drape with two closely-spaced fenestrations — a drape in which the bridging portion interposed between such fenestrations is capable of withstanding the forces which might be expected to occur during any of the aforementioned operative procedures despite the non-woven and somewhat fragile nature of the paper material from which the drape is formed and despite the close spacing of the two fenestrations.

Other advantages and objects will become more apparent from the specification and drawings.

DRAWINGS

DESCRIPTION

Figure 1:
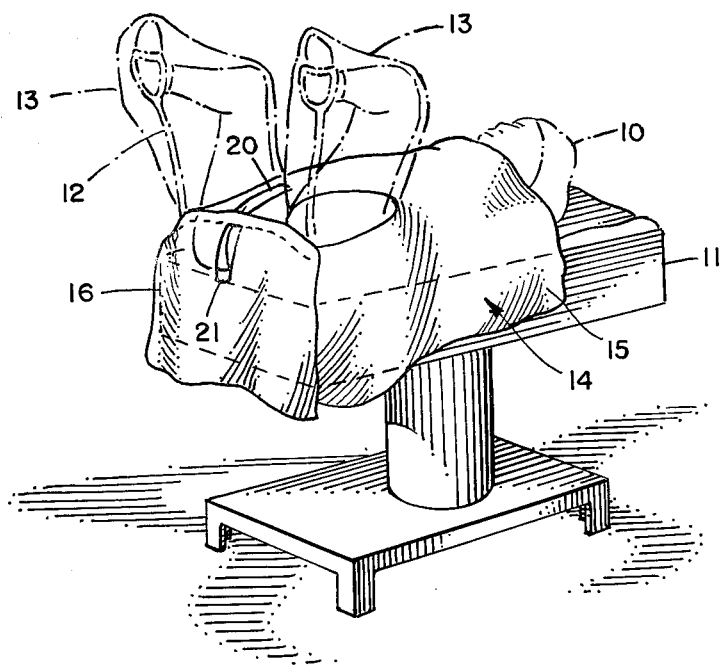
FIG. 1 is a perspective view illustrating a drape embodying the invention applied to a patient in the lithotomy position on an operating table.

Referring to the drawings, FIG. 1 illustrates a patient supported upon operating table 11 with legs held in raised position by stirrups 12. The legs are draped with suitable leggings of the type well known in the art and disclosed in patents such as U.S. Pat. Nos. 3,030,957 and 3,037,507; since such leggings form no part of the present invention, they are illustrated only in phantom.

Figure 2:
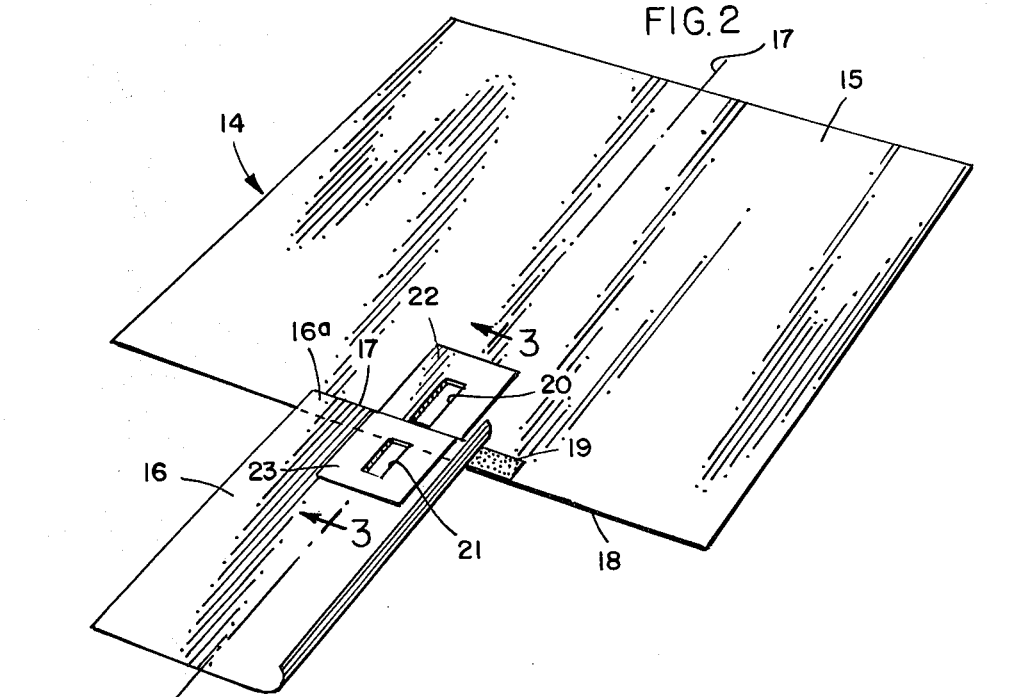
FIG. 2 is a perspective view of the drape with one of the sheets rolled back along one edge to illustrate more clearly the laminated construction thereof.

The fenestrated surgical drape is generally designated by the numeral 14 and, as shown most clearly in FIG. 2, comprises a relatively large rectangular main body sheet 15 and a smaller rectangular secondary sheet 16, both being formed of a soft water-resistant non-woven cellulosic material which is relatively strong and tear resistant, even when wet, and which may include in its structure a grid or scrim of reinforcing filaments formed of nylon, cotton, or other suitable natural or synthetic material. Such material, which is sometimes referred to as "paper" herein, is now widely used in the fabrication of surgical drapes. Since the material is known and in common use, and is described in the aforementioned patents and elsewhere, a more detailed description is believed unnecessary here.

Each sheet 15 and 16 is symmetrically oriented with respect to the drape's longitudinal midline 17. Sheet 16 has a narrow portion 16a along one transverse marginal edge 17 that is disposed in overlapping relation with regard to a like portion 15a of sheet 15 extending along transverse edge 18. The overlapping portions are secured together by adhesive 19 as illustrated in the schematic sectional view of FIG. 3. It is to be understood that any of a variety of commercially available adhesives may be used and that other suitable bonding agents or means for securing the sheets in overlapping relation might also be employed. The overlapping bonded relationship of the sheets results in substantial reinforcement in the narrow zone of lamination extending transversely between fenestrations 20 and 21.

Figure 3:
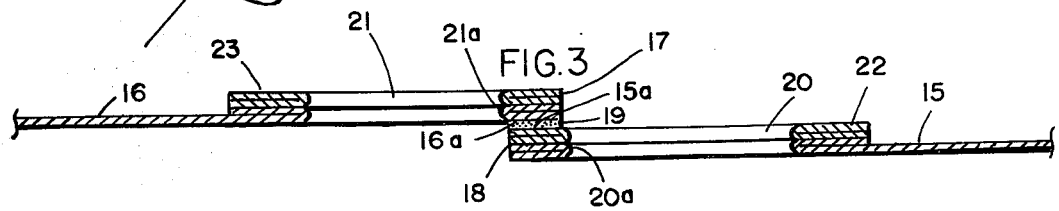
FIG. 3 is an enlarged somewhat schematic longitudinal sectional view taken along line 3—3 of FIG. 2.

The fenestrations 20 and 21 are longitudinally elongated and are preferably rectangular in shape. As shown in the drawings, they are arranged in longitudinal alignment along midline 17 on opposite sides of the transversely-extending overlapping zone between portions 15a and 16 a. Each sheet has its fenestration immediately adjacent to the marginal edge of the other sheet secured thereto. Thus, as illustrated in FIG. 3, edge 21a of fenestration 21 is closely positioned with respect to marginal edge 18 of the main sheet, whereas edge 20a of fenestration 20 is close to marginal edge 17 of the smaller sheet.

Small rectangular reinforcing panels 22 and 23 are preferably secured to sheets 15 and 16 by a suitable adhesive or bonding agent. The panels may be formed from cellulosic material of the type already described and are both arranged on the same side of the drape as illustrated. The edges of the panels and of the sheets which extend about fenestrations 20 and 21 are folded in a manner commonly used in forming the fenestrations of paper surgical drapes and illustrated in FIG. 3. As a result, the edges defining the fenestrations are relatively smooth, non-linting, and non-fraying.

While in the foregoing, an embodiment of the invention has been disclosed in considerable detail for purposes of illustration, it will be understood by those skilled in the art that many of these details may be varied without departing from the spirit and scope of the invention.

I claim:

1. A reinforced surgical drape comprising a pair of sheets of non-woven cellulosic material, one of said sheets having a narrow portion along one marginal edge thereof secured in overlapping relation to a like portion of the other of said sheets to provide a laminated zone of mutual reinforcement, said sheets having a pair of elongated fenestrations arranged in longitudinal alignment on opposite sides of said zone, each sheet having its fenestration immediately adjacent to the said marginal edge of the other sheet secured thereto.

2. The drape of claim 1 in which said narrow portion extends along the full length of said marginal edge of one of said sheets and along substantially less than the full length of said marginal edge of the other of said sheets.

3. The drape of claim 1 in which said sheets are each generally rectangular in shape, one of said sheets being substantially wider than the other of said sheets.

4. The drape of claim 3 in which said sheets are symmetrically oriented with respect to the longitudinal midline of said drape, said laminated zone of reinforcement extending across said midline and said elongated fenestrations extending along said midline.

5. The drape of claim 4 in which each of said fenestrations is generally rectangular in shape and is provided with side and end edges, each fenestration having one end edge immediately adjacent said zone of reinforcement.

6. The drape of claim 1 in which said sheets are adhesively laminated together along said zone of reinforcement.

7. The drape of claim 1 in which said sheets are formed of air-permeable water-resistant paper.

* * * * *